(12) United States Patent
Kuenstner

(10) Patent No.: US 9,451,914 B2
(45) Date of Patent: Sep. 27, 2016

(54) INTEGRATED NEEDLE AND TEST STRIP ASSEMBLY AND METHOD OF USE

(75) Inventor: J. Todd Kuenstner, Charleston, WV (US)

(73) Assignee: Charleston Area Medical Center, Inc., Charleston, WV (US)

( * ) Notice: Subject to any disclaimer, the term of this patent is extended or adjusted under 35 U.S.C. 154(b) by 1196 days.

(21) Appl. No.: 13/452,462

(22) Filed: Apr. 20, 2012

(65) Prior Publication Data

US 2013/0172780 A1 Jul. 4, 2013

Related U.S. Application Data

(63) Continuation-in-part of application No. 13/342,649, filed on Jan. 3, 2012, now Pat. No. 8,628,724.

(51) Int. Cl.
*A61B 5/00* (2006.01)
*A61B 5/157* (2006.01)
(Continued)

(52) U.S. Cl.
CPC ............. *A61B 5/157* (2013.01); *A61B 5/1411* (2013.01); *A61B 5/150022* (2013.01); *A61B 5/15105* (2013.01); *A61B 5/15142* (2013.01); *A61B 5/150358* (2013.01); *A61B 5/150389* (2013.01); *A61B 5/150419* (2013.01);
(Continued)

(58) Field of Classification Search
CPC ................ A61B 5/1411; A61B 5/145; A61B 5/150022; A61B 5/157; A61B 5/15105
USPC ....... 422/82.01, 68.1, 76; 600/573, 583, 584
See application file for complete search history.

(56) References Cited

U.S. PATENT DOCUMENTS

| 4,883,068 A | * | 11/1989 | Dechow | A61B 5/1411 600/573 |
| 5,231,993 A | | 8/1993 | Haber et al. | |
| 5,377,674 A | | 1/1995 | Kuenstner | |

(Continued)

FOREIGN PATENT DOCUMENTS

| WO | WO9708987 A1 | 3/1997 |
| WO | WO9710745 A1 | 3/1997 |

OTHER PUBLICATIONS

S.A. Williams, S. Wasserman, D.W. Rawlinson, R.I. Kitney, L.H. Smaje and J.E. Tooke, "Dynamic measurement of human capillary blood pressure," Clinical Science, 74, 507-512, 1988.

(Continued)

*Primary Examiner* — Max Hindenburg
*Assistant Examiner* — Jonathan M Foreman
(74) *Attorney, Agent, or Firm* — Spilman Thomas & Battle, PLLC; Eric D. Ruka

(57) ABSTRACT

Methods and systems to collect a sample of bodily fluid from a patient using an integrated needle and test strip assembly are provided. The test strip and needle form one unit that captures the sample of blood or interstitial fluid from the patient once the apparatus is pressed to the skin. The hollow needle includes more than one opening at a distal end, each opening coming into contact with the bodily fluid when disposed within a cutaneous or subcutaneous layer of the patient's skin. The sample may flow through the needle onto a test region by capillary action and/or the positive pressure of the bodily fluid (e.g. blood or interstitial fluid) relative to the external environment. The disclosed test strip includes at least one reaction site for testing analyte concentrations and a means for interfacing with many commercially available test strip meters to provide readout of the analyte concentration.

18 Claims, 8 Drawing Sheets

(51) Int. Cl.
*A61B 5/15* (2006.01)
*A61B 5/151* (2006.01)
(52) U.S. Cl.
CPC .. *A61B 5/150503* (2013.01); *A61B 5/150717* (2013.01); *A61B 5/150969* (2013.01)

(56) References Cited

U.S. PATENT DOCUMENTS

| | | | | |
|---|---|---|---|---|
| 5,478,328 | A * | 12/1995 | Silverman | A61M 5/32 604/110 |
| 5,505,212 | A * | 4/1996 | Keljmann | A61B 5/1411 600/573 |
| 5,636,640 | A * | 6/1997 | Staehlin | A61B 5/1411 600/577 |
| 5,692,503 | A | 12/1997 | Kuenstner | |
| 6,071,294 | A * | 6/2000 | Simons | A61B 5/1411 606/181 |
| 6,393,310 | B1 | 5/2002 | Kuenstner | |
| 6,660,527 | B2 | 12/2003 | Stroup | |
| 6,780,651 | B2 * | 8/2004 | Douglas | B01L 3/5023 422/401 |
| 7,335,166 | B2 | 2/2008 | Faupel et al. | |
| 8,025,628 | B2 | 9/2011 | Wong et al. | |
| 2005/0015019 | A1 | 1/2005 | Honda et al. | |
| 2005/0245844 | A1 * | 11/2005 | Mace | A61B 5/1411 600/583 |
| 2008/0154107 | A1 | 6/2008 | Jina | |
| 2010/0256524 | A1 | 10/2010 | Levinson et al. | |

OTHER PUBLICATIONS

C. Izquierdo and F.J. Burguillo, "Synthetic Substrates for Thrombin," Int. J. Biochem., vol. 21, No. 6, pp. 579-592, 1989.

H. Fruhstorfer and T. Mueller, "Capillary blood sampling: how much pain is necessary? Part1: Comparison of existing finger stick devices," Practical Diabetes International, vol. 12 No. 2 Mar./Apr. 1995.

A.C. Shore et al, "Capillary pressure, pulse pressure amplitude, and pressure waveform in healthy volunteers," American Journal of Physiology, 268, No. 1 part 2:H147-, 1995.

Daisuke Yamada, Fujio Sekiya, and Takashi Morita, "Isolation and Characterization of Carinactivase, a Novel Prothrombin Activator in Echis carinatus Venom with a Unique Catalytic Mechanism," vol. 271, No. 9, pp. 5200-5207, 1996.

John P. Bantle and William Thomas, "Glucose measurement in patients with diabetes mellitus with dermal interstitial fluid," The Journey of Laboratory and Clinical Medicine, 130, issue 4: 436-441, Oct. 1997.

Michael E. Collison, Phillip J. Stout, Tatyana S, Glushko, Kristen N. Pokela, Debra J Mullins-Hirte, Joel R. Racchini, Melissa A. Walter, Steve P. Meca, Joanna Rundquist, John J. Allen, Michael E. Hilgers and Thomas B. Hoegh, "Analytical characterization of electrochemical biosensor test strips for measurement of glucose in low-volume interstitial fluid samples," Clinical Chemistry, 45: 1665-1673, 1999.

Phillip Stout, Kristen Pokela, Debra Mullins-Hirte, Michael E. Hilgers, Ann Thorp, Michael E. Collison and Tatyana Glushko, "Site-to-site variation of glucose in interstitial fluid samples and correlation to venous plasma glucose," Clinical Chemistry 45: 1674-1675, 1999.

Suresh N, Thennadil, Jessica L. Rennert, Brain J, Wenzel, Kevin H. Hazen, Timothy L. Ruchti and Marshal B, Block, "Comparison of glucose concentration in interstitial fluid, and capillary and venous blood during rapid changes in blood glucose levels," Diabetes Technology & Therapeutics, 3, issue 3: 357-365, 2001.

David Cohen, "Painless needle copies mosquito's stinger," New Scientist, 11:38, Apr. 4, 2002; www.newscientist.com, Apr. 4, 2012.

John M. Ellison, et al., "Rapid changes in postprandial blood glucose produce concentration differences at finger, forearm and thigh sampling sites," Diabetes Care, 25, No. 6: 961-964, 2002.

Zachary T. Bloomgarden, "blood glucose monitoring," Medscape Today, Oct. 13, 2003.

Miyakoshi, M. Kamoi, K. Iwanaga, M. Hoshiyama, A. Yamada, A., "Comparison of patient's preference pain perception & visibility between Micro Fine Plus 31-gauge needle and microtapered Nano Pass 33-gauge needle for insulin therapy," J Diabetes Sci Technol, 1(5): 718-724, Sep. 2007.

N.S. Oliver, et al., Glucose sensors: a review of current and emerging technology, Diabetic Medicine, 26: 197-210, 2009.

Stanley Kim, "A Pain-free Lancet with a Small Needle for Glucose Measurement," Clinical Medicine insights: Endocrinology and Diabetes, 3 1-7, 2010.

Sander S. Van Berkel, Bas Van Der Lee, Floris L. Van Delft, Rob Wagenvoord, H. Coenraad Hemker, and Floris P.J.T. Rutjes, "Fluorogenic Peptide-Based Substrates for Monitoring Thrombin Activity," ChemMedChem 7, 6006-617, 2012.

* cited by examiner

INTEGRATED NEEDLE AND TEST STRIP ASSEMBLY AND METHOD OF USE

CROSS-REFERENCE TO RELATED APPLICATIONS

The present patent application is a continuation-in-part of co-pending U.S. patent application Ser. No. 13/342,649, filed Jan. 3, 2012, which is incorporated herein by reference.

STATEMENT REGARDING FEDERALLY SPONSORED RESEARCH

Not Applicable.

THE NAMES OF THE PARTIES TO A JOINT RESEARCH AGREEMENT

Not Applicable.

INCORPORATION-BY-REFERENCE OF MATERIAL ON DISC

Not Applicable.

BACKGROUND

1. Technical Field of the Invention

This invention pertains generally to an analyte test strip assembly for use in diagnostic testing for an analyte concentration. More specifically, the invention pertains to an integrated needle and test strip assembly, the needle having a central hollow-bore and at least one transverse hollow-bore. The integrated needle and test strip assembly may use capillary action to collect a sample of blood or interstitial fluid cutaneously or subcutaneously from a patient and, in conjunction with an analyte meter, measure an analyte concentration.

2. Background of the Invention

Electronic testing systems are commonly used to measure or identify one or more analytes in a sample. Such testing systems can be used to evaluate medical samples for diagnostic purposes and to test various non-medical samples. For example, medical diagnostic meters can provide information regarding presence, amount, or concentration of various analytes in human or animal body fluids. In addition, diagnostic test meters can be used to monitor analytes or chemical parameters in non-medical samples such as water, soil, sewage, sand, air, or any other suitable sample.

Diagnostic testing systems typically include both a test medium, such as a diagnostic test strip, and a test meter configured for use with the test medium. Suitable test media may include a combination of electrical, chemical, and/or optical components configured to provide a response indicative of the presence or concentration of an analyte to be measured. For example, some glucose test strips include electrochemical components, such as glucose specific enzymes, buffers, and one or more electrodes. The glucose specific enzymes may cause a reaction between glucose in a sample and various chemicals on a test medium, thereby producing an electrical signal that can be measured with the one or more electrodes. The test meter can then convert the electrical signal into a glucose test result.

Diagnostic testing systems have improved significantly in recent years. For example, test meters have become smaller and faster, and the amount of blood or other fluid needed to obtain accurate test results has decreased. However, although these improvements have made testing more convenient for patients, current systems have some drawbacks. For example, current systems and devices for monitoring blood glucose levels in diabetic patients require three separate devices; a lancet, a blood glucose meter, and test strips. The need to carry these three items can be inconvenient and cumbersome. In addition, carrying more components makes it easier to misplace or lose a component. Further, the current systems frequently employ lancets which can be reused. Reusing the same lancet is less sanitary than using a new, disposable lancet each time and can cause the lancet to become dull over time, leading to more pain for the patient upon use.

The pain associated with the use of a lancet is a constant concern for diabetic patients. The overall objective of the lancet is to cause a wound that will produce blood on the surface of the skin. Current lancets use a myriad of different engagement devices to create the wound. The most common method involves the use of a spring loaded lancet strike to breach the patient's skin and thereby insert the lancet. This unpleasant method has substantial drawbacks such as lancet needle movement, vibration or misapplication of force by the lancet triggering device, all of which lead to increased pain for the patient.

Since the advent of these point of care testing systems in the 1970s ("Glucose sensors: a review of current and emerging technology," N. S. Oliver, et. al., *Diabetic Medicine*, 26:197-210, 2009; incorporated herein by reference), a non-invasive method of determining an analyte concentration such as glucose has been intensively sought and researched. To date the search has not yet resulted in a United States FDA approved device of acceptable accuracy (N. S. Oliver, et. al.). Other analytes of greater concentration have been shown to be amenable to noninvasive testing, for example, carboxyhemoglobin, as described in U.S. Pat. Nos. 5,692,503 and 6,393,310 B1, and hemoglobin, as described in U.S. Pat. No. 5,377,674 for total hemoglobin, all to this inventor. Devices are now being sold that measure these analytes non invasively.

However, the search for a noninvasive method for the measurement of other analytes such as, for example, glucose has proven more elusive. As such, while the current methods and systems facilitate the self-monitoring of analyte concentrations in blood or bodily fluid, there is need for additional features and improvements, including systems with fewer components, less painful blood or interstitial fluid collection, more precise fluid collection methods for elderly or less dexterous patients, and less cumbersome and cleaner fluid collection methods. The present invention overcomes many of the shortcomings of the prior art of lancets and test strips.

SUMMARY

According to its major aspects, and briefly stated, the present invention includes a method and system for collection of a sample of blood or interstitial fluid from a patient using a hollow-bore mini-needle which is integrated with a test strip. Reagents on the test strip may react with an analyte in the sample, and in conjunction with an analyte meter, measure the analyte content. The sample may pass through the needle to the test strip using capillary action and/or the positive pressure of the bodily fluid (e.g. blood or interstitial fluid) relative to the external environment. The needle may contain one or more transverse hollow-bores allowing for more than one point of entry for the sample. Further, the needle may contact and collect the sample at a subcutaneous level so that no bodily fluid is expressed to the surface of the patient's skin.

A first embodiment of the present invention is directed to an integrated needle assembly for collection of a sample. The needle assembly may comprise: a needle having an upper flange, a distal end, a central hollow-bore extending through at least a portion of the needle, and at least one transverse hollow-bore in fluid communication with the central bore; and a sensor strip containing at least one reaction reagent for determining a concentration of at least one analyte in the sample, the sensor strip having at least one port for passage of the upper flange of the needle. The needle assembly may be used to collect a sample of bodily fluid through the needle using capillary action or the positive internal pressure of the bodily fluid relative to the external environment. The needle may pierce a subcutaneous or cutaneous layer of a patient's skin creating a channel for the bodily fluid to pass. The more efficient sample collection may permit a smaller volume of sample to be collected for analysis, which may be obtained from a smaller needle inflicted wound with consequently less pain. The methods and systems disclosed herein require less manual dexterity by a user and entail less pain for the patient during the collection process.

The needle assembly may further comprise a needle guide having at least one port for passage of the needle; and a user deployment cover. Further, the sensor strip may contain at least one reaction reagent for determining a concentration of at least one analyte in the sample, the sensor strip disposed between the user deployment cover and the needle guide. The needle assembly may further comprise an analyte reaction assembly disposed between the user deployment cover and the needle guide and configured to contain the sensor strip within a reaction region.

In embodiments, the needle assembly may further comprise a fluid filter permeable to gas but not fluids disposed between the sensor strip and the user deployment cover.

In embodiments, the analyte reaction assembly may comprise an insulating substrate having an electrical terminal at a first end; a first conductor disposed on the insulating substrate extending from the electrical terminal to the sensor strip; a second conductor disposed on the insulating substrate extending from the electrical terminal to the sensor strip; and an insulating layer disposed on the insulating substrate, first conductor, and second conductor. In embodiments, the insulating substrate may include a void passing therethrough configured to contain the sensor strip.

In embodiments, the user deployment cover may comprise at least one transparent region. In further embodiments, the user deployment cover may comprise markings which direct a user to apply pressure to a region of the needle assembly.

In embodiments, the needle guide may further comprise an adhesive layer adjacent to the needle to impede horizontal and vertical movement of the needle assembly during use. Furthermore, the needle guide thickness may be used to determine or guide the depth of penetration of the needle during use.

In embodiments, the integrated needle assembly for collection of a sample may further comprise a protective needle cover removably disposed over the needle guide adhesive layer, the protective needle cover maintaining a sterile environment for the needle, reaction region of the analyte reaction assembly, sensor strip and needle guide.

In embodiments, the sample may comprise blood or dermal interstitial fluid. Furthermore, the needle may be about 0.2 mm to 1.0 mm in length and about 25 gauge to 35 gauge in diameter. In embodiments, the volume of the sample may be about 0.3 microliters to about 30 microliters.

In embodiments, the analyte tested using the needle assembly may be a sugar, glucose, lactate, fructosamine, glutamine, a ketone, pyruvate, 3-hydroxybutyric acid, acetyl choline, cholesterol, peroxide, a protein, prostate-specific antigen, prothrombin, thromboplastin, fibrinogen, hemoglobin, myoglobin, albumin, troponin, C-reactive protein, amylase, alanine transaminase, aspartate transaminase, alkaline phosphatase, creatine kinase, a peptide, brain natriuretic peptide (proBNP), a break-down product of metabolism, creatinine, bilirubin, uric acid, a hormone, luteinizing hormone, chorionic gonadotropin, thyroid stimulating hormone, a drug, an antibiotic, gentamicin, vancomycin, digitoxin, digoxin, barbiturates, methadone, amphetamine and amphetamine analogues, propoxyphene, opiates, cocaine, tetrahydrocannabinol, benzodiazepines, phencyclidine, theophylline, warfarin, a virus, a bacterium, or a coagulate. In yet further embodiments, the analyte tested may be glucose and a reaction reagent in the sensor strip may be glucose oxidase or glucose dehydrogenase. In yet further embodiments, the analyte tested may be prothrombin and a reaction reagent in the sensor strip may be at least one of carinactivase-1, calcium ions and an indicator such as, for example, a peptidylarginine p-nitroanilide or peptidyl-7-amido-4-methylcoumarin.

A second embodiment of the present invention is directed to an integrated needle and test strip assembly for collection of a sample. The needle assembly may comprise: a needle having an upper flange, a distal end, a central hollow-bore extending through the needle, and at least one transverse hollow-bore in fluid communication with the central bore; and a test strip containing at least one sensor region, wherein the sensor region may contain at least one reaction reagent for determining a concentration of at least one analyte in the sample, the sensor region in fluid communication with the upper flange of the needle.

A third embodiment of the present invention is directed to a method of using an integrated needle and test strip assembly. The method comprises pressing the distal end and at least one transverse bore of a needle having an upper flange, a distal end, a central hollow-bore extending through at least a portion of the needle, and at least one transverse hollow-bore near the distal end in fluid communication with the central bore into skin of a patient; and holding the needle in place until a sample is drawn through the needle into a test strip in fluid communication with the needle, the test strip containing at least one reaction reagent for determining a concentration of at least one analyte in the sample. In embodiments, the method may further comprise removing a protective needle cover from the integrated needle and test strip assembly before pressing the distal end of the needle into the skin of the patient.

BRIEF DESCRIPTION OF THE DRAWINGS

Aspects, features, benefits and advantages of the embodiments herein will be apparent with regard to the following description, appended claims, and accompanying drawings. In the following figures, like numerals represent like features in the various views. It is to be noted that features and components in these drawings, illustrating the views of embodiments of the present invention, unless stated to be otherwise, are not necessarily drawn to scale.

DETAILED DESCRIPTION

Figure 1:
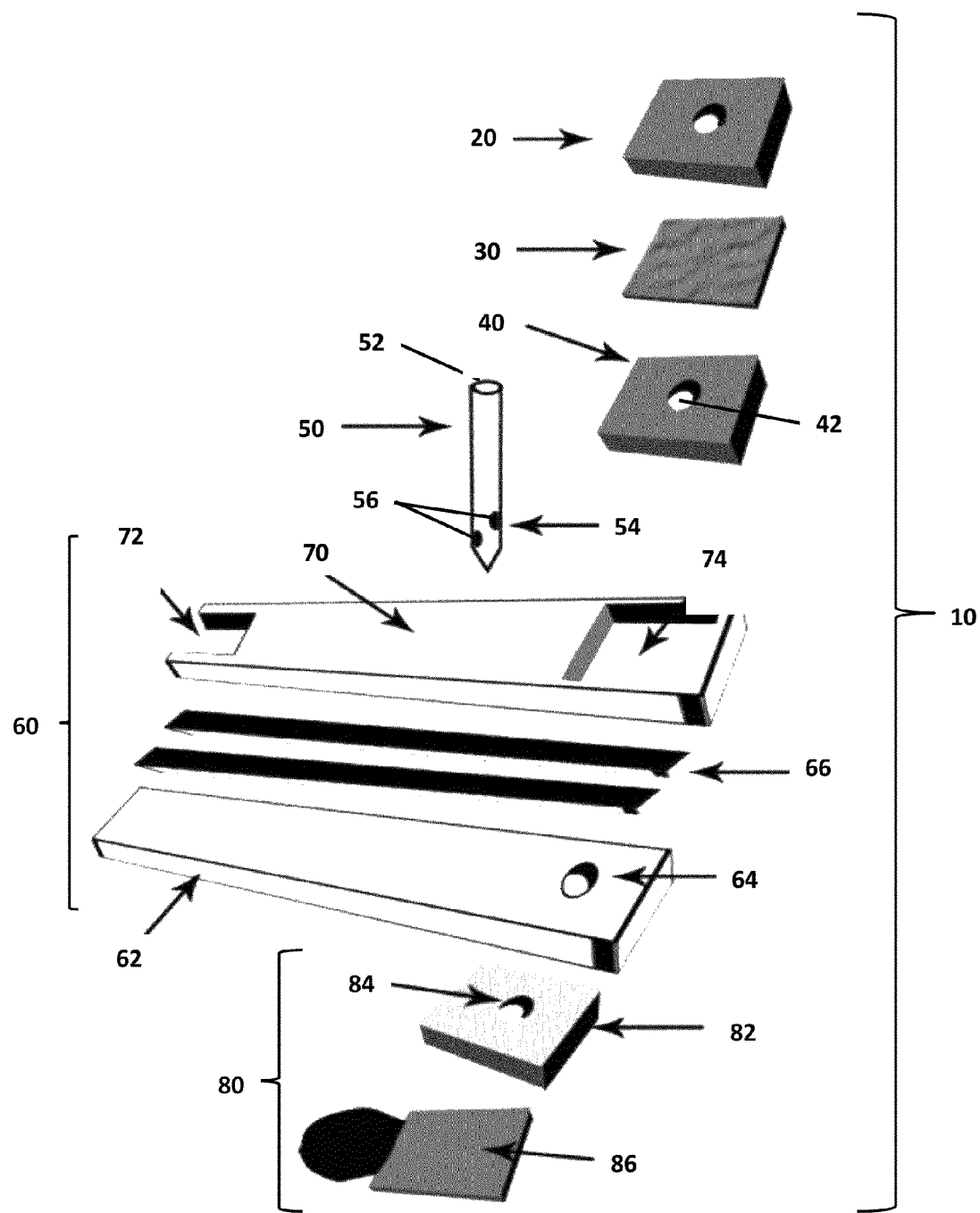
FIG. 1 illustrates an exploded view of an integrated needle and test strip assembly using capillary action to collect a sample in accordance with certain aspects of the present invention.

In the following description, the present invention is set forth in the context of various alternative embodiments and implementations involving an integrated needle and test strip assembly which may allow a sample of bodily fluid from a patient to be collected and tested. The needle assembly may be used to collect a sample of blood or interstitial fluid cutaneously or subcutaneously from the patient and, in conjunction with an analyte meter, measure an analyte content of the collected blood or interstitial fluid. The sample may be collected onto a test region of the integrated needle and test strip assembly by capillary action and/or the positive pressure of the bodily fluid (e.g. blood or interstitial fluid) relative to the external environment. The needle assembly may provide a single needle having more than one opening at a distal end, each opening coming into contact with the bodily fluid when disposed within a cutaneous or subcutaneous layer of the patient's skin. Further, the needle assembly may provide more than one needle, wherein each needle may have more than one opening at a distal end, each opening coming into contact with the bodily fluid when disposed within a cutaneous or subcutaneous layer of the patient's skin. In accordance with aspects of the present invention, the integrated needle and test strip assembly may be mated to an analyte meter configured to automatically begin the metering process as the bodily fluid is collected into the assembly.

Various aspects of the integrated needle and test strip assembly may be illustrated by describing components that are coupled, attached, and/or joined together. As used herein, the terms "coupled", "attached", and/or "joined" are interchangeably used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements shown in said examples.

Various aspects of the integrated needle and test strip assembly may be illustrated with reference to one or more exemplary implementations. As used herein, the term "exemplary" means "serving as an example, instance, or illustration," and should not necessarily be construed as preferred or advantageous over other variations of the devices, systems, or methods disclosed herein. "Optional" or "optionally" means that the subsequently described event or circumstance may or may not occur, and that the description includes instances where the event occurs and instances where it does not. In addition, the word "comprising" as used herein means "including, but not limited to".

Furthermore, throughout the specification, reference to "one embodiment," "an embodiment," or "some embodiments" means that a particular described feature, structure, or characteristic is included in at least one embodiment. Thus, appearances of the phrases "in one embodiment," "in an embodiment," or "in some embodiments" in various places throughout this specification are not necessarily all referring to the same embodiment. Those skilled in the art will recognize that the various embodiments can be practiced without one or more of the specific details or with other methods, components, materials, etc. In other instances, well-known structures, materials, or operations are not shown or not described in detail to avoid obscuring aspects of the embodiments.

Relative terms such as "lower" or "bottom" and "upper" or "top" may be used herein to describe one element's relationship to another element illustrated in the drawings. It will be understood that relative terms are intended to encompass different orientations of aspects of the integrated needle and test strip assembly in addition to the orientation depicted in the drawings. By way of example, if aspects of the integrated needle and test strip assembly shown in the drawings are turned over, elements described as being on the "bottom" side of the other elements would then be oriented on the "top" side of the other elements as shown in the relevant drawing. The term "bottom" can therefore encompass both an orientation of "bottom" and "top" depending on the particular orientation of the drawing.

It must also be noted that as used herein and in the appended claims, the singular forms "a", "an", and "the" include the plural reference unless the context clearly dictates otherwise. Thus, for example, reference to an "orifice" is a reference to one or more orifices and equivalents thereof known to those skilled in the art, and so forth. Unless defined otherwise, all technical and scientific terms used herein have the same meanings as commonly understood by one of ordinary skill in the art.

It will be appreciated that the following embodiments and implementations are illustrative and various aspects of the invention may have applicability beyond the specifically described contexts. Furthermore, it is to be understood that these embodiments and implementations are not limited to the particular components, methodologies, or protocols described, as these may vary. The terminology used in the description is for the purpose of illustrating the particular versions or embodiments only, and is not intended to limit their scope in the present disclosure which will be limited only by the appended claims.

Referring now to the drawings, embodiments of the integrated needle and test strip assembly of the present invention are shown in FIGS. 1-7 generally designated by the reference numeral 10. FIG. 1 illustrates an exploded view of an embodiment of the integrated needle and test strip assembly 10 which may include a user deployment cover 20, a fluid filter 30, a sensor strip 40, a needle 50, an analyte reaction assembly 60, and a needle guide and protection assembly 80. The assembly 10 provides a single integrated unit that may allow a user to collect a sample of bodily fluid by pushing the needle 50 through a barrier layer on a patient. The needle 50 may then provide a transport channel for the sample to the sensor strip 40 for estimation of an analyte concentration using the analyte reaction assembly 60 in conjunction with a commercial test strip meter.

The needle 50 may be a hollow aspiration needle, for example, having a central hollow-bore extending from a distal end 54 or from near the distal end 54 to an opening in a needle flange 52. The distal end 54 of the needle 50 may be used to penetrate the barrier layer and provide a pathway for collection of a sample from beneath the barrier layer onto the sensor strip 40. For example, the needle 50 may be used to pierce a patient's skin so that a sample of blood or interstitial fluid may be collected from the distal end 54 through the central hollow-bore onto the sensor strip 40. The needle is thus serving the dual purpose of fluid sampler, or lancet, and collection channel.

This dual purpose of the needle of the present invention—fluid sampler and collection channel—simplifies the use of the integrated needle and test strip assembly 10. As discussed previously, current diagnostic test systems necessitate a separate lancet which creates a wound in the patient's skin and allows a sample of bodily fluid to pool on the surface of the skin. The pooled sample of fluid is then captured onto a test region by capillary action. Not only does this two-step system generate more sample than may be required, the sample is exposed to air and other contaminants prior to collection. The patient is left with a pool of sample, most commonly blood, which is not used for testing and must be cleaned. Furthermore, most current lancet systems use a mechanical spring loaded actuator to trigger the lancet's entry into the patient's skin. Such systems enter the skin layer rapidly, come to an abrupt stop and then quickly retract. These combined abrupt actions not only cause a significant amount of pain for the patient, but also cause the wound channel to collapse, trapping some or all of the bodily fluid beneath the skin. As a result, the patient must apply pressure to milk the sample to the surface of the skin. The needle 50 of the integrated needle and test strip assembly 10 of the present invention solves these problems.

In embodiments, the needle 50 of the integrated needle and test strip assembly 10 does not use an actuator. Rather, the needle 50 may be pressed through the barrier layer on a patient using pressure, for example, on the user deployment cover 20. The needle may further be held in place on the barrier layer by an adhesive on the needle guide 82 so that the wound channel remains open during sample collection.

The sample may be collected onto the sensor strip 40 by capillary action alone or in combination with the positive pressure of the bodily fluid relative to the external environment. Capillary action is the ability of a fluid to be drawn up into a hollow tube or narrow space without assistance. The height of a liquid in a hollow tube, such as the hollow-bore needle 50 described herein, may be given by the equation $$h = \frac{2\gamma \cos\theta}{\rho g r},$$

where $\gamma$ is the liquid-air surface tension, $\theta$ is the contact angle of the fluid with the tube wall, $\rho$ is the density of the liquid, g is the gravitational field strength, and r is the radius of the tube. For a water filled tube at standard atmospheric conditions, $\gamma=0.0728$ N/m at 20° C., $\theta=20°$, $\rho$ is $1000$ kg/m$^3$, and g=9.81 m/s$^2$. Thus, in a 0.4 mm tube water would rise 2.8 inches. For blood, a density or $\rho$ of 1060 kg/m$^3$ may be used to find that blood would rise about 2.6 inches in a 0.4 mm tube (i.e. a tube of diameter comparable to a 27 gauge needle) corresponding to a volume of 33 microliters. As will be discussed below, current diagnostic methods for analyte determination typically require sample volumes as small as 0.5 microliters to 2.0 microliters. Thus, capillary action would provide more than enough sample volume for accurate testing in the integrated needle and test strip assembly 10.

The human capillary system maintains a measurable positive pressure that would further aid in sample collection. As reported in the article "Capillary pressure, pulse pressure amplitude, and pressure waveform in healthy volunteers," A. C. Shore et. al., *American Journal of Physiology*, 268, number 1 part 2:H147-, 1995, capillary pressure in the fingertip ranges between 15.9 mmHg for women and 18.2 mmHg for men. Furthermore, capillary pressures may be as high as 40 mmHg in the arm or leg, as reported by S. A. Williams in the article "Dynamic measurement of human capillary blood pressure," *Clinical Science* (London), 74, number 5:507-512, 1988. Such capillary pressures would provide a force equivalent to at least 0.3 pounds per square inch (based on pressure in the fingertip of a woman). These physiologic facts suggest that there may be sufficient blood pressure in the capillary bed to drive the blood through the needle 50 and into the test strip 40 in the integrated needle and test strip assembly 10.

The user deployment cover 20 may be formed to create a sealed, fluid protection barrier that may have a transparent portion 28 for the user to view a blood or interstitial fluid level in embodiments where such filling is desirable, for example. The transparent portion 28 may have dimensions matching those of a top surface of the user deployment cover 20, may be a small portion of the user deployment cover 20 as is depicted in FIG. 1, or may be the entire surface of the user deployment cover 20. Furthermore, the user deployment cover 20 may have dimensions which differ from those depicted in FIG. 1. The user deployment cover 20 may be formed from a polymer or any other suitable material, and may be flexible or rigid. In embodiments, the user deployment cover 20 may have markings which direct the user to apply pressure to a region of the integrated needle and test strip assembly 10.

In accordance with an aspect of the present invention, the needle 50 may be configured with at least one transverse hollow-bore 56, or orifice, in fluid communication with the central hollow-bore to assist collection of the sample onto the sensor strip 40. Such a design may provide several advantages. First, when used to collect a sample of blood or interstitial fluid, the orifice(s) 56 may, for example, prevent the sides of the needle 50 from tamponading blood flow from the capillaries, which may sometimes result if the only site of fluid collection is from a single point at the distal end of the needle 54. Second, the reduced surface area of such a needle 50 may elicit less pain to the patient when the needle 50 penetrates the skin. As noted in the article "Painless needle copies mosquito's stinger," David Cohen, *New Scientist*, 11: 38, Apr. 4, 2002, the entirety of which is incorporated herein by reference, the process of a mosquito removing blood from a human is essentially painless. The mosquito proboscis is highly serrated, thus reducing the surface area which is in contact with the human tissue and consequently reducing stimulation of the nerves. Third, the orifices 56 may increase the surface area in which blood or interstitial fluid enter the needle 50. This increased surface area may aid in more efficient sample collection and may be advantageous in the event of clotting of blood or blockage, for example, at the needle tip.

Figure 5:
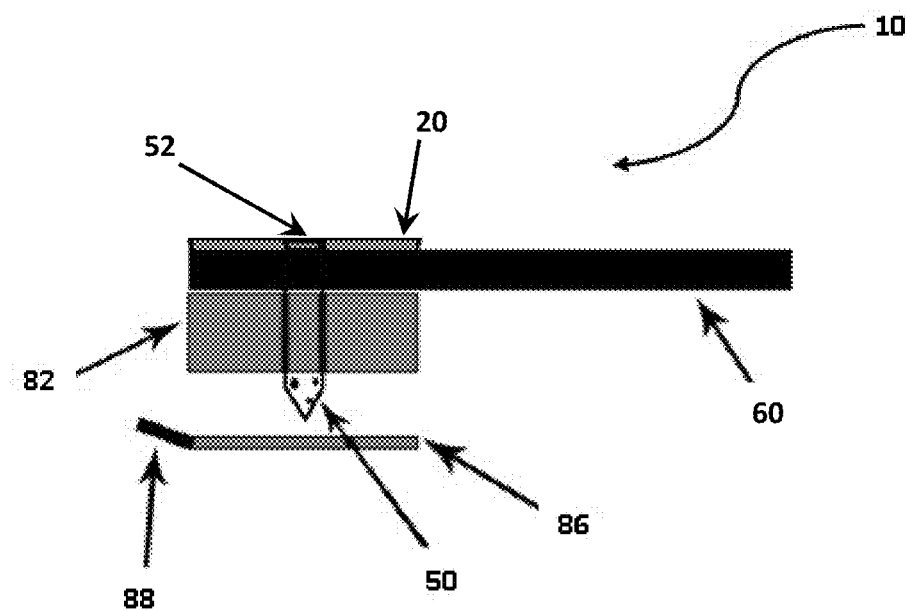
FIG. 5 illustrates a side view of an integrated needle and test strip assembly having the protective layer removed to thereby expose the needle, in accordance with certain aspects of the present invention.
Figure 6:
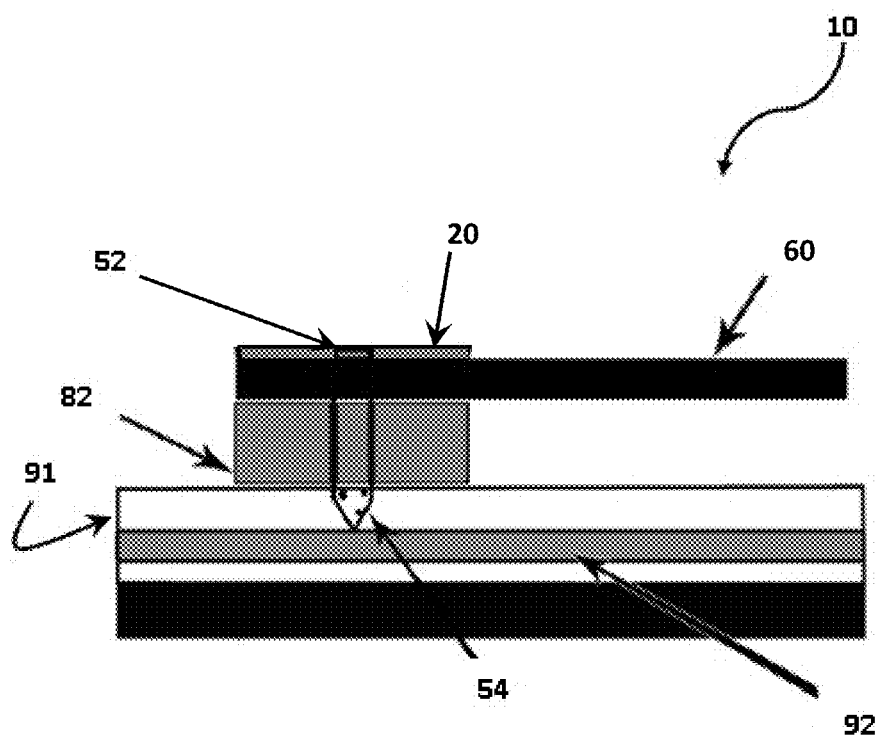
FIG. 6 illustrates a side view of an integrated needle and test strip assembly in a state of use after the apparatus contacts the patient's skin and begins to penetrate the dermal layer, but before complete depth is achieved, to illuminate a function of the needle guide, in accordance with certain aspects of the present invention.

It will be appreciated that the orifice(s) 56 in such a needle 50 may be formed in any number of different patterns on the needle 50. For example, the orifice(s) 56 may be formed in a helical (spiral) pattern along the longitudinal axis of the needle 50, or may be formed in a staggered pattern where more than one orifice 56 may lie along the same longitudinal axis. Further, the number of orifice(s) 56 may be variable and may depend on a number of different parameters, including the size of the orifice(s) 56, the size of the opening at the distal end 54 of the needle 50, the intended application in terms of the makeup and location of the sample, and the volume of sample to be collected. The spacing between the orifice(s) 56 and the distance between the distal end 54 of the needle 50 and the orifice(s) 56 may vary. Thus, while FIGS. 1, 5 and 6 are shown with a prescribed number, size and pattern of orifice(s) 56, this is merely for illustrative purposes and does not limit the present invention in any way. It will further be appreciated that the needle 50 can include only a single orifice 56 and may or may not include an opening that is formed at the distal tip 54.

As discussed above, the design of the needle 50 to include at least one orifice 56 may aid in more efficient sample collection and may thus allow the use of needles which have shorter lengths and smaller diameters. The needle 50 of the integrated needle and test strip assembly 10 may be between 0.2 mm and 1.0 mm in length and may be 25 gauge to 35 gauge in diameter. As noted in the article "Capillary blood sampling: how much pain is necessary? Part 1: comparison of existing finger stick devices," H. Fruhstorfer and T. Mueller, *Practical Diabetes* 12(2): 72-74, March/April 1995, the entirety of which is incorporated herein by reference, longer and thicker lancet designs, as used in conventional integrated test apparatuses, often elicit greater pain and collect an amount of blood that is too large. Clinical trials have shown that one of the smallest lancets on the market, the Tiniboy™, is less painful to use ("A pain-free lancet with a small needle for glucose measurement," S. Kim, *Clinical Medicine Insights: Endocrinology and Diabetes* 2010:3 1-7, the entirety of which is incorporated herein by reference). The dimensions of this lancet are 36 gauge (0.18 mm in diameter) and 0.7 mm in length (see www.tiniboy.com). Current diagnostic methods for analyte determination typically require sample volumes as small as 0.5 microliters to 2.0 microliters. Thus, the design of the integrated needle and test strip assembly 10 of the present invention may permit the use of a needle 50 which has a shorter length and smaller diameter, allowing for collection of sufficient blood or interstitial fluid with a minimum of pain for the patient.

In accordance with an aspect of the present invention, the needle 50, or a portion thereof, may be coated with a lubricant or other suitable substance to reduce friction upon insertion, thus reducing the resultant discomfort and/or permitting the use of a larger bore needle if desired. As noted in the article "Comparison of patient's preference, pain perception, and usability between Micro Fine Plus 31-gauge needle and microtapered NanoPass 33-gauge needle for insulin therapy," Miyakoshi, M. et. al., *Diabetes Sci Technol*, 1(5): 718-724, September 2007, the entirety of which is incorporated herein by reference, lubricant on the external surface of a needle may reduce discomfort during needle insertion.

In accordance with an aspect of the present invention, the sample collected using the integrated needle and test strip assembly 10 may be blood or interstitial fluid. Several published studies have shown that for several standard analyte measurements, blood and interstitial fluid showed similar results. For example, glucose measurements on interstitial fluid were practically indistinguishable from capillary blood glucose measurements (1. "Glucose measurement in patients with diabetes mellitus with dermal interstitial fluid," John P Bantle and William Thomas, *The Journal of Laboratory and Clinical Medicine*, 130, issue 4: 436-441, October, 1997. 2. "Analytical characterization of electrochemical biosensor test strips for measurement of glucose in low-volume interstitial fluid samples," Michael E. Collison, et. al., *Clinical Chemistry*, 45: 1665-1673, 1999. 3. "Site-to-site variation of glucose in interstitial fluid samples and correlation to venous plasma glucose," Phillip Stout, et. al., *Clinical Chemistry* 45: 1674-1675, 1999.), each reference being incorporated herein by reference. Further, an additional article showed that there is no time lag of glucose concentration between interstitial fluid and capillary blood ("Comparison of glucose concentration in interstitial fluid, and capillary and venous blood during rapid changes in blood glucose levels," Suresh N. Thennadil, et. al., *Diabetes Technology & Therapeutics*, 3, issue 3: 357-365, 2001; incorporated herein by reference.)

The needle 50 of the integrated needle and test strip assembly 10 of the present invention may be used to penetrate a barrier layer on a patient. In embodiments, the barrier layer is a cutaneous or subcutaneous layer of skin on the patient's body, preferably at the fingertip. As discussed above, the design of the needle 50 to include at least one orifice 56 and to be of short length (between 0.2 and 1.0 mm) and small diameter (25 to 35 gauge) allows for less painful collection of the sample. When used in the fingertip to collect a sample of blood or interstitial fluid, this provides a great advantage. While the fingertip has more nerve endings, capillary blood is more plentiful, as noted in the article "Blood glucose monitoring," Zachary T. Bloomgarden, *Medscape Today*, Oct. 13, 2003, incorporated herein by reference. Furthermore, during conditions of rapidly changing analyte concentration, there may be a time delay difference with venous blood which is evident at alternate test sites, such as the forearm or thigh for example, but is not evident with fingertip sampling of capillary blood, as discussed in the article "Rapid changes in postprandial blood glucose produce concentration differences at finger, forearm and thigh sampling sites," John M. Ellison, et. al., *Diabetes Care*, 25, number 6: 961-964, 2002, incorporated herein by reference.

In accordance with other aspects of the present invention, although referred to herein as a needle, the needle 50 may be a lancet or a combination lancet and hollow needle, having a solid portion and/or a hollow portion, or any combination thereof.

In accordance with an aspect of the present invention, one or more one-way or check valves (not shown) may be included in the integrated needle and test strip assembly 10, at a predetermined location(s) between the distal end 54 of the needle 50 and the sensor strip 40. These one-way valves may ensure that fluid or gas does not enter into the patient's body from the exterior environment (i.e. the integrated needle and test strip assembly) when the needle 50 pierces the patient's skin. Rather, only bodily fluid(s) may flow out of the wound into the distal end 54 of the needle 50 and onto the sensor strip 40. For example, a one-way valve may be integrated into the needle flange 52, or provided at any other location along the fluid path from an inlet at the distal end 54 of the needle 50 to an inlet into the sensor strip 40.

In embodiments, a fluid filter 30 may be situated between the user deployment cover 20 and the sensor strip 40, the fluid filter 30 being configured to allow air or gas to pass while preventing any collected fluid from being drawn into the user deployment cover 20 viewing window 28. The filter 30 may also provide a method to hold the collected bodily fluid on a chemical reaction layer of the sensor strip 40 and may thus improve reaction with the reaction reagents on the sensor strip 40. In certain embodiments, the fluid filter 30 may be disposed beneath the sensor strip 40 adjacent an analyte reaction region 74. In such an embodiment, the fluid filter 30 may comprise a port (not shown) for passage of the needle 50 and may be oriented so that the gas-only permeable side faces away from the sensor strip 40. In such an embodiment, the fluid filter 30 may allow the sample of bodily fluid to be held in proximity to the chemical reaction layer of the sensor strip 40 while discouraging excess flow of the bodily fluid into the analyte reaction region 74 in the direction of the distal end 54 of the needle 50.

As shown in FIG. 1, the analyte reaction assembly 60 may be constructed by forming a sandwich of several layers of electrically insulating substrates. For example, a first insulating substrate 62 may contain a supply port 64 to hold the needle 50 inline and anchored within the analyte reaction assembly 60. Two or more electrodes 66 may be glued, affixed or printed onto the insulating substrate 62. An additional insulating layer 70 may be adhered or affixed to the first insulating substrate 62 so that the electrodes 66 may be effectively sandwiched between the two layers. This second insulating layer 70 may contain a cutout portion 72 that allows at least a portion of each of the electrodes 66 to remain exposed for mating the analyte reaction assembly 60 to an analyte meter. That is, the electrodes 66 may extend from the analyte reaction assembly 60 out of the integrated needle and test strip assembly 10 and may be attached to an analyte meter, which may be designed to accept the integrated needle and test strip assembly 10 of the present invention. The second insulating layer 70 may also contain a cutout section which defines an analyte reaction region 74, configured to hold the sensor strip 40 when the integrated needle and test strip assembly 10 is assembled. At least a portion of the electrodes 66 may be exposed at the analyte reaction region 74.

In embodiments, the sensor strip 40 may contain reaction reagents that allow the integrated needle and test strip assembly 10 to test the content of an analyte in the sample. Readout of the results of such a test may be provided when the integrated needle and test strip assembly 10 is attached to an analyte meter. During use, the sample collected by the integrated needle and test strip assembly 10 may contain an analyte which becomes mixed with one or more reaction reagents in the sensor strip 40. The reaction reagent may dissolve in the sample solution (e.g. if the reagents exist in a dry state on the sensor strip) and/or become mixed with the sample solution (e.g. if the reagents exist in a liquid state on the sensor strip) allowing the analyte to become oxidized or reduced by the reaction reagent. The concentration of the analyte in the sample solution may be determined based on the electrical current produced by the oxidation/reduction reaction which is sensed at the electrodes 66. As such, measurement of various analytes in the sample is possible if a suitable corresponding reaction reagent is selected. For example, if the integrated needle and test strip assembly 10 is used to measure a glucose concentration in a patient's blood sample, at least one of the reaction reagents may be glucose oxidase or glucose dehydrogenase.

The analyte tested on the sensor strip 40 of the integrated needle and test strip assembly 10 may be a chemical compound or organic molecule such as, for example, a sugar, glucose, lactate, fructosamine, glutamine, a ketone, pyruvate, 3-hydroxybutyric acid, acetyl choline, cholesterol or peroxide. The analyte tested may be a protein or enzyme such as, for example, prostate-specific antigen, prothrombin, hemoglobin, myoglobin, albumin, troponin, C-reactive protein, amylase, alanine transaminase, aspartate transaminase, alkaline phosphatase or creatine kinase. The analyte tested may be a peptide such as, for example, brain natriuretic peptide (proBNP). The analyte tested may be a break-down product of metabolism such as, for example, creatinine, bilirubin or uric acid. Further, the analyte tested may be a hormone such as, for example, luteinizing hormone, chorionic gonadotropin or thyroid stimulating hormone. The analyte tested may be a drug, such as, for example, an antibiotic (e.g., gentamicin, vancomycin, and the like), digitoxin, digoxin, a drug of abuse (e.g., barbiturates, methadone, amphetamine and amphetamine analogues, propoxyphene, opiates, cocaine, tetrahydrocannabinol, benzodiazepines, phencyclidine, and the like), theophylline or warfarin. The analyte tested may be a virus or bacterium. The analyte tested may be a coagulate, such as from a blood sample when mixed with thromboplastin or thrombin. In embodiments, the analyte tested may be glucose and a reaction reagent in the sensor strip may be glucose oxidase or glucose dehydrogenase.

In embodiments, the integrated needle and test strip assembly 10 may use photometric rather than electrochemical means to detect a signal indicative of an analyte concentration in the sample of patient's bodily fluid. The analyte in the sample may mix with reaction reagents on the sensor strip 40 or may remain unreacted (i.e. unchanged). The analyte reaction assembly 60 may thus be constructed without electrodes 66, but may instead provide a means for allowing the reacted or unreacted analyte on the sensor strip 40 to be analyzed or detected by an analyte meter. Detection may be by any photometric means known in the art such as, for example, a shift in wavelength, a change in reflectance, transmittance, absorbance, fluorescence, luminescence or phosphorescence. In embodiments, the analyte in the sample may mix with reaction reagents on the sensor strip 40 that cause a color change which may be readable by the user or patient. As such, results of an analyte test using the integrated needle and test strip assembly 10 may be determined directly without attachment to an analyte meter.

In embodiments, the integrated needle and test strip assembly 10 may be used to measure a prothrombin concentration in a patient's blood sample using photometric means. Prothrombin is a vitamin K-dependent plasma protein that is needed for the normal clotting of blood. When activated, prothrombin undergoes proteolytic cleavage at two sites to yield thrombin. Thrombin is in turn a protease which converts soluble fibrinogen to insoluble fibrin to produce the initial visible demonstration of coagulation, the soluble fibrin clot. In the presence of vitamin K antagonists, such as sodium warfarin (also known as COUMADIN®), or in the absence of vitamin K, prothrombin activity in the blood can be significantly diminished. Severe liver disease may also be linked to low plasma prothrombin activity. Thus, impaired synthesis of proteins (liver disease), inadequate supplies of vitamin K (vitamin K deficiency), or drugs that inhibit the action of vitamin K (sodium warfarin) lead to diminished plasma prothrombin activity.

Embodiments of the integrated needle and test strip assembly 10 may contain at least one reaction reagent on the sensor strip 40 capable of measuring prothrombin levels in whole blood. Such reaction reagents may include at least one of carinactivase-1 and calcium ions, as discussed in the article "Isolation and characterization of Carinactivase, a novel prothrombin activator in *Echis carinatus* venom with a unique catalytic mechanism," Daisuke Yamada et. al., *The Journal of Biological Chemistry*, 271, number 9:5200-5207 1996, incorporated herein by reference. In the presence of calcium, carinactivase-1 cleaves prothrombin to thrombin. Thrombin concentrations may then be determined using thrombin's ability to cleave fluorogenic or chromogenic peptide based substrates such as peptidyl 7-amino-4-methylcoumarin ("Fluorogenic peptide-based substrates for monitoring thrombin activity," Sander Berkel et. al., *Chem Med Chem*, 7:606-617, 2012, incorporated herein by reference) or peptidyl ρ-nitoanilide ("Synthetic substrates for thrombin," C. Izquierdo et. al., *International Journal of Biochemistry*, 21, number 6:579-592, 1989, incorporated herein by reference). In such an embodiment, the integrated needle and test strip assembly 10 may use photometric rather than electrochemical means to detect the fluorogenic or chromogenic signal indicative of the prothrombin concentration in the sample of the patient's blood.

The integrated needle and test strip assembly 10 may be constructed by extending the needle 50 through the analyte reaction region 74 and the supply port 64 of the analyte reaction assembly 60 so that the distal end 54 of the needle 50 is held in place by, and protrudes from a lower surface of, the first insulating substrate 62. In this manner, the needle 50 may be configured to protrude a predetermined distance, accommodating varying needle lengths and gauges, such as needles having a protruding length of 0.2 mm to 1.0 mm and having a gauge of 25 to 35, for example. The sensor strip 40, which may be wholly composed of a reaction reagent chemical composition deposited into the analyte reaction region 74, for example, may form a test layer duct 42 designed to further stabilize the needle 50 and to seat the needle flange 52. Moreover, the analyte reaction region 74 of the second insulating layer 70 may be configured to not only hold the sensor strip 40, but to also allow direct communication between the analyte chemicals of the sensor strip 40 and the electrodes 66.

The needle 50 may thus be stabilized and mounted into the analyte reaction assembly 60 with the needle flange 52 situated in a manner to collect fluid onto the analyte chemical layer of the contained sensor strip 40. The fluid filter 30 and the user deployment cover 20 may then be mounted, such as by adhesive or heat seal, for example, onto the analyte reaction assembly 60. The cutout section 74 may be configured, for example, to seat the user deployment cover 20 with the sensor strip 40 effectively sealed with the user deployment cover 20 at the top and the electrodes/first insulating substrate 62 at the bottom. The sensor strip 40 would thus be completely contained in the analyte reaction region 74 in a sealed environment, preventing contamination of the analyte chemical layer and ensuring a substantially aseptic environment for the testing of the patient's blood or interstitial fluid.

The analyte chemical layer of the sensor strip 40 may be a small region of the sensor strip 40, a single layer within the sensor strip 40, or may occupy the entire sensor strip 40. Similarly, different chemicals or reaction components may occupy different regions of the sensor strip 40. In embodiments which use photometric rather than electrochemical means to detect a signal indicative of an analyte concentration in the sample of patient's bodily fluid, the sensor strip 40 may contain further indicator chemicals. In certain embodiments, the integrated needle and test strip assembly 10 may be configured without a sensor strip 40, but may have reaction reagents in a liquid form for reaction with the analyte to be tested in the sample of bodily fluid. Such reagents may be held within the analyte reaction region 74, or within any other portion of the analyte reaction assembly 60. In such embodiments, various viewing windows may be configured within the analyte reaction assembly 60 for detection and analysis of the analyte concentration.

The needle guide and protection assembly 80 may be provided to protect the distal end 54 of the needle 50 during transport and handling while preventing contamination of the aseptically contained sensor strip 40. The assembly 80 may include, for example, a needle guide 82 and a protective needle cover 86. The needle guide 82 may be configured to have a needle duct 84. Further, in embodiments, the needle guide 82 may be composed of a deformable material, such as foam, that may compress when the integrated needle and test strip assembly 10 is pressed to the patient's skin. As such, the needle 50 may be entirely encased within the needle duct 84 of the needle guide 82 and covered by the needle cover 86 when the integrated needle and test strip assembly 10 in not in use. Thus, the needle 50 would only be exposed after the user removed the needle cover 86 and pressed the integrated needle and test strip assembly 10 into the skin, compressing the foam of the needle guide 82 so that the needle 50 may protrude into the patient's skin.

The needle guide 82 may be further configured to have an adhesive coating on a bottom side (facing the protective needle cover) which may serve to hold the protective needle cover 86 in place prior to use of the integrated needle and test strip assembly 10. To ensure the assembly 10 has not been accessed prior to use, a tamper indicator may be included on the protective needle cover 86. For example, a perforation may be positioned over a seam formed at the edges of the protective needle cover 86, such as at an edge congruent with the needle guide 82. A ripped or torn perforation could then indicate that the assembly 10 has been opened and that the needle 50 may no longer be sterile. While a perforation is mentioned as a possible tamper indicator, any means for providing a tamper evident seal known in the art may be used and is within the scope of the present invention.

The adhesive coating on the needle guide 82 may also provide a means for holding the integrated needle and test strip assembly 10 in place during use on a patient. As mentioned previously, most current lancet systems use a mechanical spring loaded actuator to trigger the lancet's entry into the patient's skin. Movement and vibrations of the lancet, once actuated, have been shown to stimulate nerve sensors beneath the skin and cause pain for the patient, as discussed in the article "Capillary blood sampling: how much pain is necessary? Part 1: relationship between penetration depth and puncture pain," H. Fruhstorfer et. al., *Practical Diabetes* 12(4): 184-185, March/April 1995, the entirety of which is incorporated herein by reference. Further, such movement may allow the wound channel to collapse, thus reducing the ability to collect a sample. The adhesive coating on the needle guide 82 may allow the integrated needle and test strip assembly 10 to remain in place during sample collection, thus reducing any movement of the needle 50 once deployed within the patient's cutaneous or subcutaneous layer. Furthermore, the present integrated needle and test strip assembly 10 may simply be pressed into the patient's cutaneous or subcutaneous layer, for example the patient's fingertip, using another finger.

Figure 2:
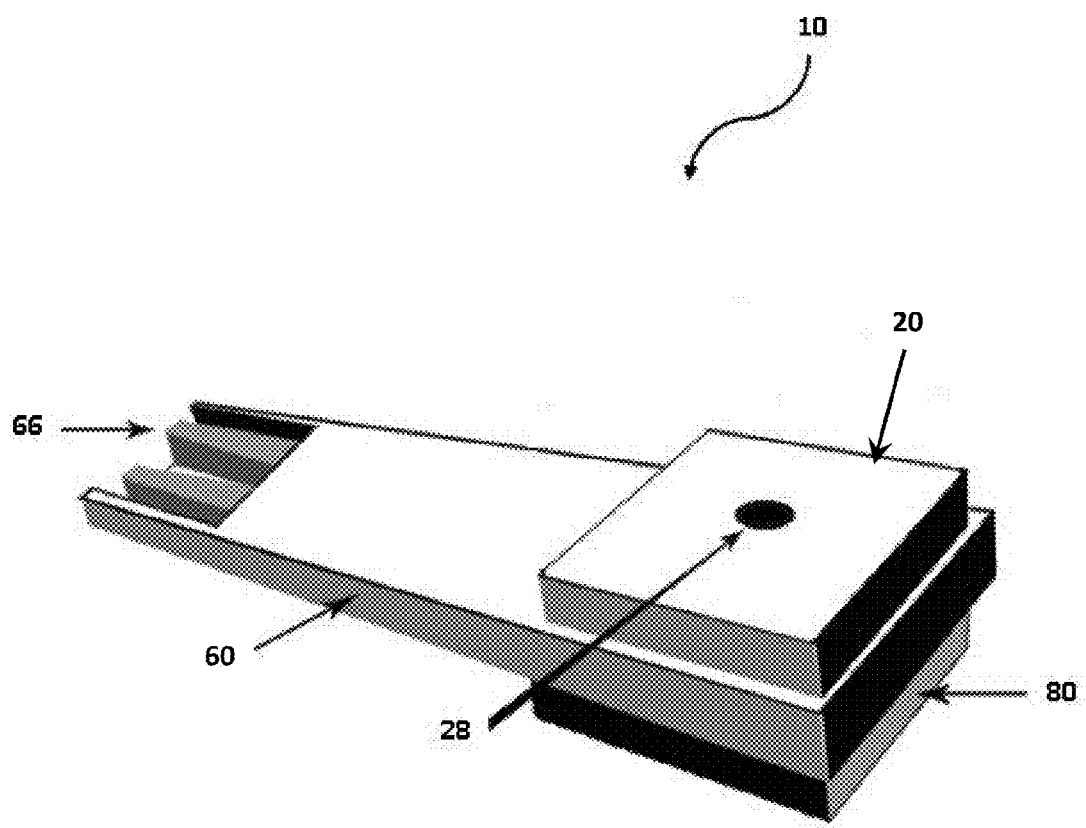
FIG. 2 illustrates a front view of an integrated needle and test strip assembly, showing an electrode system used to connect to a digital reader, a location for an uppermost flange of the needle, and a user deployment cover, in accordance with certain aspects of the present invention.

FIG. 2 illustrates a perspective view of the integrated needle and test strip assembly 10 as assembled. The analyte reaction assembly 60 in this embodiment is sandwiched between the user deployment cover 20 and the needle guide and protection assembly 80. The sensor strip 40 is self-contained in the interior of the integrated needle and test strip assembly 10 and may be visible, for example, by using transparent materials for aspects of the apparatus, including, for example, the components of the user deployment cover 20, as is depicted by the viewing port 28. The electrodes 66 are exposed and ready for easy and efficient connection of the integrated needle and test strip assembly 10 to an analyte meter or suitable device for reading the results of the chemical reaction that will occur when the sample of bodily fluid is collected onto the sensor strip 40.

In accordance with an aspect of the present invention, a patient's blood or interstitial fluid is collected cutaneously or subcutaneously and does not need to propagate to the surface of the skin. Through the use of the needle 50 disclosed herein, the fluid sample is collected directly onto the sensor strip 40 of the analyte reaction assembly 60, controlling the flow of the bodily fluid and sealing the pressure differential to the wound after a sufficient, predetermined amount of bodily fluid is collected. As such, the patient may not observe any bodily fluid on the surface of the skin once the fluid has been collected. Thus, the discomfort to the patient will be minimized and the possibility of dealing with blood or interstitial fluid spillage is reduced.

The ability to collect a predetermined amount of bodily fluid cutaneously or subcutaneously provides a myriad of advantages to the testing process as the chemical reaction can be contained with little opportunity of contamination or misapplication of fluid sample onto the sensor strip 40. The disclosed integrated needle and test strip assembly 10 allows for the reading of an analyte concentration in either a photometric or electrochemical manner, for example, hence providing a flexibility to use existing test strip readers and simply adapting the disclosed assembly 10 to commercially available readers rather than creating a new reader or developing a differently shaped test strip.

In embodiments, the integrated needle and test strip assembly 10 may be made to visually appear substantially similar to current test strip designs, for example, thereby providing a sense of continuity to patients that already use a certain brand or style of test strip. The disclosed integrated needle and test strip assembly 10 may simplify the patient's daily fluid collection process while enhancing the accuracy of that process.

Figure 3:
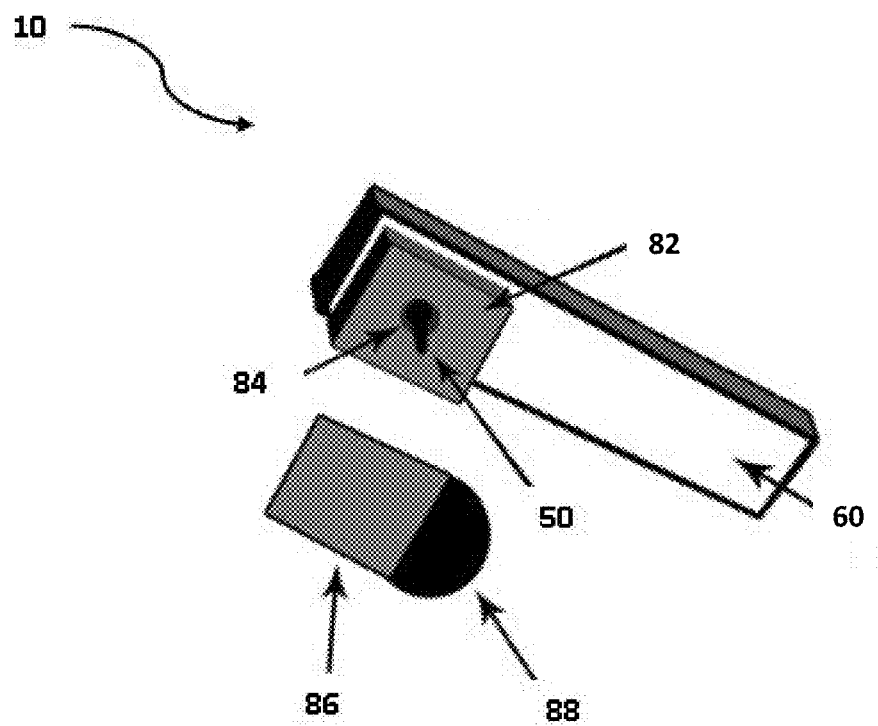
FIG. 3 illustrates a bottom view of an integrated needle and test strip assembly having a protective layer removed to expose the needle centered within a needle guide, in accordance with certain aspects of the present invention.

FIG. 3 illustrates a bottom perspective view of the integrated needle and test strip assembly 10. The needle 50 may extend from the needle duct 84 of the needle guide 82, or may be entirely encased within the needle duct 84 as discussed above. The protective needle cover 86, which may be adhesively applied, for example, may protect the exposed portion of the needle 50 and further prevent contaminants from entering into the interior of the integrated needle and test strip assembly 10. A finger positioning flap 88 may be provided to allow the protective needle cover 86 to be easily and ergonomically detached from the needle guide 82.

Figure 4:
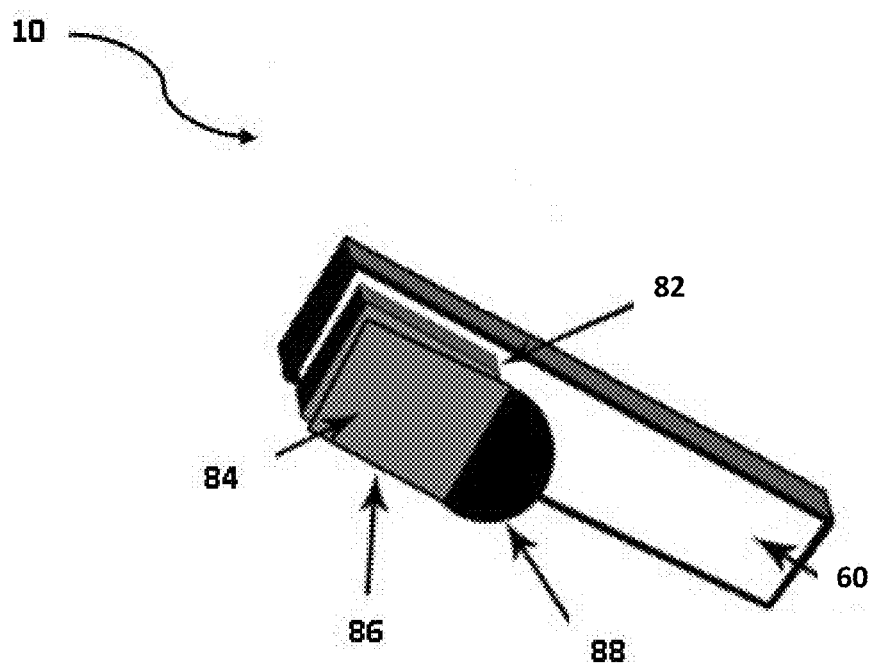
FIG. 4 illustrates a bottom view of an integrated needle and test strip assembly having the protective layer attached to thereby protect a user from accidental sticks/pricks, provide for sterile protection of the needle, and for use in discarding, in accordance with certain aspects of the present invention.

FIG. 4 illustrates a bottom perspective view of the integrated needle and test strip assembly 10, wherein the protective needle cover 86 is affixed onto the needle guide 82 to provide a protective barrier. As shown, the integrated needle and test strip assembly 10 is configured so the user is not susceptible to sticks or pricks from the needle 50 when the protective needle cover 86 is affixed. In addition, the integrated needle and test strip assembly 10 may be more readily packaged, stored, shipped, and handled without the threat of damage or tearing as a result of the needle 50.

FIG. 5 shows the integrated needle and test strip assembly 10 from a side view perspective. While the distal end 54 of the needle 50 is shown to protrude from the needle guide 82, the thickness of the needle guide 82 may be varied so that the needle 50 protrudes more or not at all. The protective needle cover 86 is shown in the removed position. The user deployment cover 20 is also shown. Any fluid collected by the needle 50 may be deposited onto the sensor strip 40 of the analyte reaction assembly 60 by virtue of the predetermined positioning of the uppermost needle flange 52. For example, the needle 50 may be positioned so that the blood or interstitial fluid is released from the opening of the needle flange 52 onto an upper layer of the sensor strip 40, or the opening of the needle flange 52 may be situated slightly lower into the test layer duct 42 (see FIG. 1) to release the blood or interstitial fluid into a more central region or even onto a lower surface of the analyte chemical layer of the sensor strip 40.

FIG. 6 shows the integrated needle and test strip assembly 10 from a side view perspective, showing the patient's skin 91 penetrated by the distal end 54 of the needle 50 with the needle guide 82 seated firmly against the surface of the skin and the user deployment cover 20 having not yet been engaged. The patient's blood or interstitial fluid 92 is shown within the skin 91 and the distal end 54 of the needle 50 has not penetrated deeply enough to collect a sample of the fluid 92. Without the user applying pressure to the user deployment cover 20, the needle 50 may not penetrate deeply enough to position the distal end 54 within the blood or interstitial fluid containing tissue.

Figure 7:
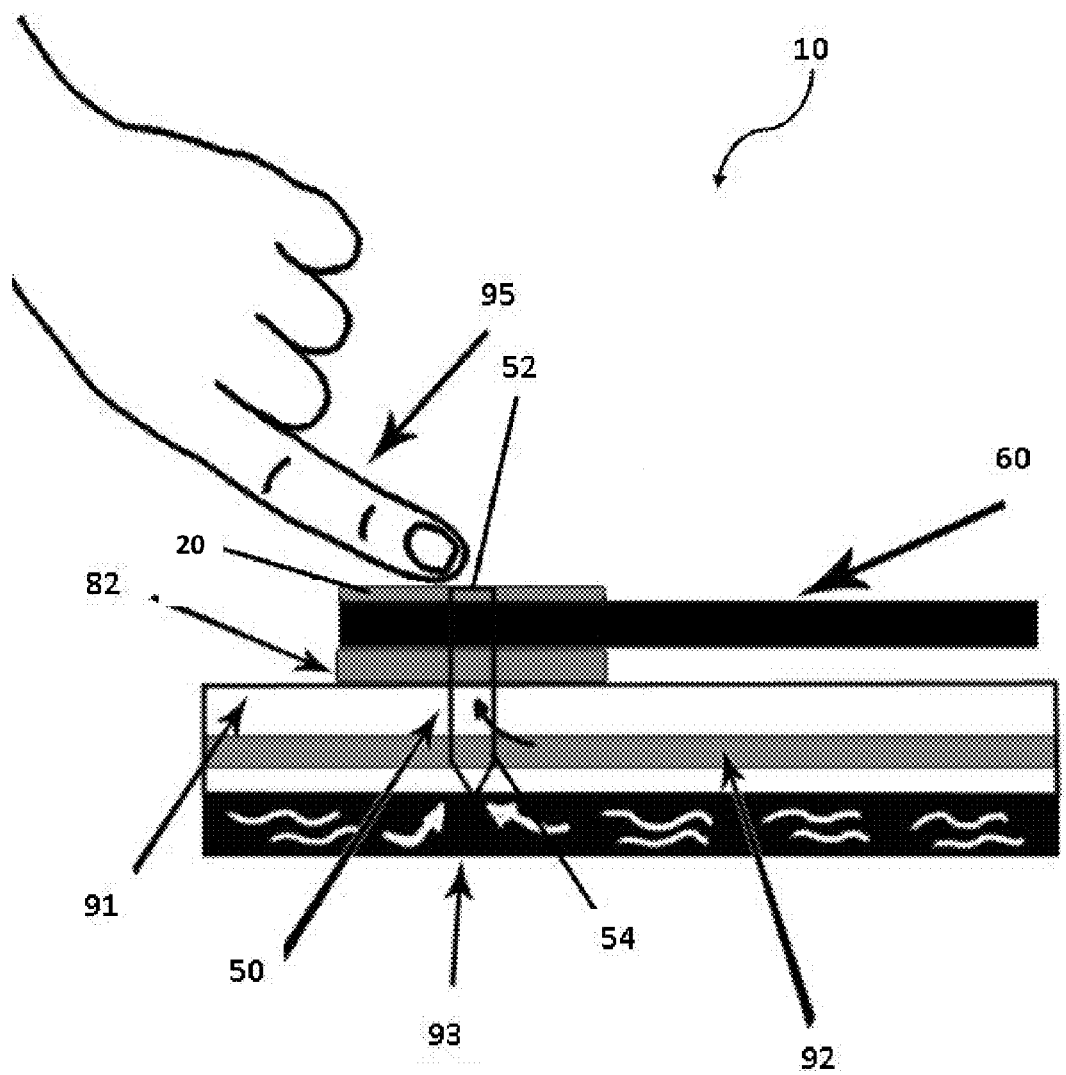
FIG. 7 illustrates a side view of an integrated needle and test strip assembly in a state of use during which the user applies pressure to the user deployment cover with full penetration of the needle in the patient's dermal layer to demonstrate collection of bodily fluid into the needle while being simultaneously deposited onto the sensor strip within the reaction region of the analyte reaction assembly, in accordance with certain aspects of the present invention.

FIG. 7 illustrates the integrated needle and test strip assembly 10 and the user 95 applying pressure to the user deployment cover 20. Blood or interstitial fluid 92 from the blood containing tissue 93 may be drawn from the distal end 54 and any orifice(s) 56 of the needle 50 to the needle flange 52 by capillary action for release onto the sensor strip 40. The needle guide 82 may be further squeezed or compressed against the patient's skin 91 under the pressure applied by the user on the user deployment cover 20, allowing the needle 50 to penetrate the skin at a substantially perpendicular angle, for example, to the integrated needle and test strip assembly 10.

In accordance with an aspect of the present invention, the needle guide 82 may be an interchangeable and configurable component. In embodiments, the integrated needle and test strip assembly 10 may be configured with any one of a variety of needle guides 82, wherein each needle guide 82 may have a different thickness, for example. Accordingly, without changing the length of the needle 50, the depth to which the needle 50 may penetrate the skin 91 can be adjusted by simply changing to a different needle guide 82, or selecting an integrated needle and test strip assembly 10 having the desired thickness of needle guide 82 already mounted. In this manner, it may be extremely easy to account for the many variations of a patient, such as age and/or skin thickness.

Figure 8:
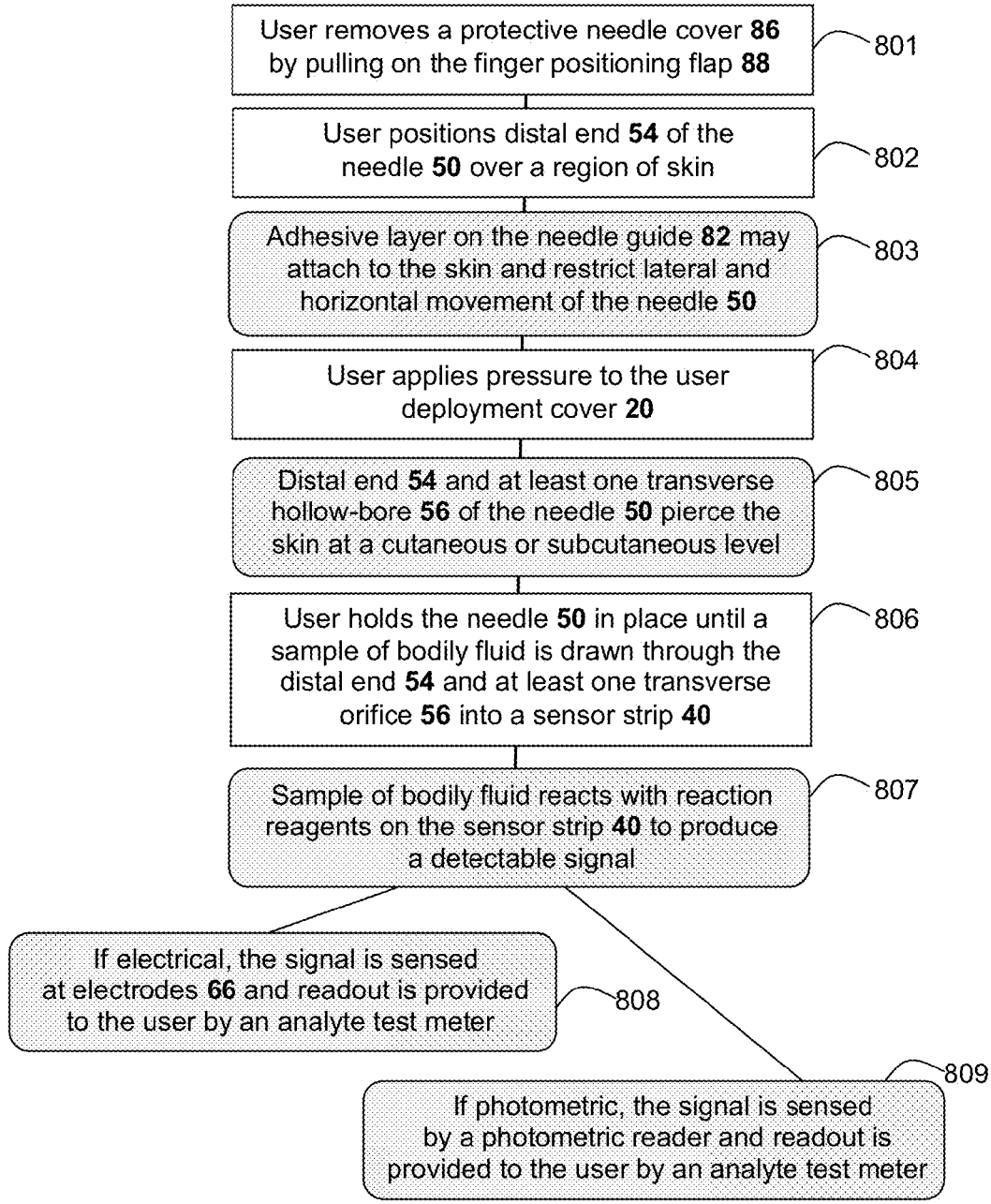
FIG. 8 depicts an exemplary flow diagram of a method of use of an integrated needle and test strip assembly, in accordance with certain aspects of the present invention.

FIG. 8 depicts an exemplary flow diagram describing one embodiment of a method of the present invention. At step 801, the user removes a protective needle cover 86 from the integrated needle and test strip assembly 10. The user may use the finger positioning flap 88 to aid in the easy and ergonomic detachment of the protective needle cover 86 from the needle guide 82. At step 802, the user positions the distal end 54 of the needle 50 over a region of skin where testing will occur such as, for example, the fingertip. Step 803 indicates that an adhesive layer on the needle guide 82 may become attached to the skin at the test site and restrict lateral and horizontal movement of the needle 50. The user then applies pressure to the user deployment cover 20 of the integrated needle and test strip assembly 10, as shown at step 804. Step 805 indicates that the distal end 54 of the needle 50 and at least one transverse hollow-bore or orifice 56 pierce the patient's skin at a cutaneous or subcutaneous level. The user may then hold the needle 50 in place by maintaining pressure on the user deployment cover 20 for a specified time, as shown at step 806. Typically, the user may hold the needle 50 in place until an adequate sample of bodily is collected onto the sensor strip 40.

Capillary action may draw a sample of bodily fluid in through the distal end 54 and at least one orifice 56 of the needle 50 and up the central hollow-bore to the upper flange 52, where the sample may flow onto the sensor strip 40. The fluid filter 30, which may be located at a position above the sensor strip 40, allows gas but not fluid to pass to the user deployment cover 20. As such, the fluid filter 30 may capture excess bodily fluid that is collected and may further aid in reaction on the sensor strip 40 by holding a reservoir of sample in contact with the sensor strip 40. As mentioned above, in certain embodiments, the fluid filter 30 may be positioned below the sensor strip 40, or may be omitted entirely from the integrated needle and test strip assembly 10. Once the sample of bodily fluid has become introduced to the sensor strip 40, an analyte in the sample may react with reagents on the sensor strip 40, as shown at step 807. The reagents on the sensor strip may produce an electrical signal that is detected by the electrode(s) 66, as shown at step 808. This signal may be read by an analyte test meter.

In embodiments, the signal produced at step 807 may be photometric rather than electrochemical. The analyte reaction assembly 60 may thus be constructed without electrodes 66, but may instead provide a means for allowing the reacted or unreacted analyte on the sensor strip 40 to be analyzed or detected by an analyte meter. Accordingly, detection of the signal may be by spectrophotometric means rather than at electrodes, as shown in step 809. In alternative embodiments, the analyte in the sample may mix with reaction reagents on the sensor strip 40 that cause a color change which may be readable by the user or patient. As such, the signal produced at step 807 may be determined directly without attachment to an analyte meter.

Performing the above-discussed steps greatly improves the ease of sample collection and reduces the pain a patient experiences. In prior art systems it can be difficult for patients, especially for patients with limited hand dexterity, such as the elderly, to collect a sample of bodily fluid. In a typical procedure, the patient first creates an incision in the skin by lancing the skin with the lancet. Once a sufficient amount of fluid collects as a droplet on the skin, the patient has to position a test strip over the incision site such that the test strip contacts and absorbs a sufficient amount of the fluid for analysis. Usually, these droplets of fluid are quite small, and patients, especially ones with poor hand motor control, may experience great difficulty in positioning the test strip so as to collect an adequate sample from the droplet. As should be appreciated, a patient can become quickly frustrated by this procedure and, consequently, they may perform the test less often or may even quit testing altogether. The integrated needle and test strip assembly 10 of the present invention solves these problems.

In accordance with various aspects of the present invention discussed herein, an embodiment of the integrated needle and test strip assembly may comprise a needle and a test strip. The needle 50 may have an upper flange 52, a distal end 54, a central hollow-bore extending through at least a portion of the needle 50, and at least one transverse hollow-bore 56 near the distal end 54 which is in fluid communication with the central bore. The test strip, which may be in fluid communication with the upper flange 52 of the needle 50, may include a combination of electrical, chemical, and/or optical components configured to provide a response indicative of the presence or concentration of the analyte to be measured. The test strip may include a sensor strip 40 and an analyte reaction assembly 60 as described herein. In alternative embodiments, the test strip may be designed and manufactured in a manner much the same as test strips currently on the market, wherein the needle would be located in a position which would allow the sample to come into contact with a reaction region on the test strip. In embodiments, the sample may be drawn up through the central bore of the needle 50 by capillary action and/or the positive pressure of the bodily fluid (e.g. blood or interstitial fluid) relative to the external environment.

Although described herein with reference to a hollow-bore needle for withdrawing a discrete amount of blood or interstitial fluid for testing, it will be readily apparent to one of ordinary skill in the art to recognize the potential of using the integrated needle and test strip assembly 10 as a syringe. By changing the direction of the one-way valves, for example, the direction of fluid flow may easily be reversed. The user deployment cover 20 may be configured as a flexible compartment with enough space to contain a discrete volume of a liquid. By pre-filling the compartment with a medication, for example, the integrated needle and test strip assembly 10 could be used to inject the medication into a patient subcutaneously, for example. The fluid filter 30 and sensor strip 40 may be removed in such an embodiment.

The previous description is provided to enable any person skilled in the art to practice the various exemplary implementations described herein. Various modifications to these variations will be readily apparent to those skilled in the art, and the generic principles defined herein may be applied to other implementations. All structural and functional equivalents to the elements of the various illustrious examples described throughout this disclosure that are known or later come to be known to those of ordinary skill in the art are expressly incorporated herein by reference.

Embodiments of the integrated needle and test strip assembly of the present invention may be configured to have similar dimensions and electrode placement as products currently on the market. Further, embodiments of the present invention may be designed to look very similar to currently marketed products. As such, a product of the present invention may allow greater user familiarity and require less modification of the manufacturing process, which may be advantageous in the market.

It should be noted that products described in the prior art are generally much larger in size and cumbersome to use because of the need for syringe operation or due to the inclusion of a mechanical lancet actuator. As such, many prior art products can only be used at alternate test sites rather than at the fingertip. Still yet other products require actuating devices to engage the needle (rather than no actuator at all), use of multiple needles and/or incorporate large fluid reservoirs for large samples. Embodiments of the integrated needle and test strip assembly described herein overcome these drawbacks. While some prior art products have incorporated the use of micro-needles, which may cause less pain, these products require more time for sample collection. As such, consumers are likely to find the longer sample collection times with micro-needles to be unacceptable and may perform the test less often or may even quit testing altogether.

While specific embodiments of the invention have been described in detail, it should be appreciated by those skilled in the art that various modifications and alternations and applications could be developed in light of the overall teachings of the disclosure. Accordingly, the particular arrangements, systems, apparatuses, and methods disclosed are meant to be illustrative only and not limiting as to the scope of the invention.

What is claimed is:

1. A needle assembly for collection of a sample, comprising:
   a needle having an upper flange, a distal end, a central hollow-bore extending through at least a portion of the needle, and at least one transverse hollow-bore in fluid communication with the central bore;
   a needle guide having at least one port for passage of the needle;
   a user deployment cover;
   a sensor strip containing at least one reaction reagent for determining a concentration of at least one analyte in the sample, the sensor strip disposed between the user deployment cover and the needle guide, the sensor strip having at least one port for passage of the upper flange of the needle;
   an analyte reaction assembly disposed between the user deployment cover and the needle guide and configured to contain the sensor strip within a reaction region; and
   a fluid filter permeable to gas but not fluids disposed between the sensor strip and the user deployment cover.

2. The needle assembly of claim 1, wherein the analyte reaction assembly comprises:
   an insulating substrate having an electrical terminal at a first end;
   a first conductor disposed on the insulating substrate extending from the electrical terminal to the sensor strip; a second conductor disposed on the insulating substrate extending from the electrical terminal to the sensor strip; and
   an insulating layer disposed on the insulating substrate, first conductor, and second conductor.

3. The needle assembly of claim 2, wherein the insulating substrate includes a void passing therethrough and wherein the sensor strip is disposed in the void.

4. The needle assembly of claim 2, wherein the insulating layer comprises the reaction region of the analyte reaction assembly, the reaction region defined by a cutout section, the cutout section to seat the user deployment cover to seal the sensor strip between the user deployment cover and the insulating substrate.

5. The needle assemble of claim 4, wherein at least a portion of each of the first conductor and the second conductor is exposed to the reaction region.

6. The needle assembly of claim 1, wherein the user deployment cover comprises at least one transparent region.

7. The needle assembly of claim 1, wherein the user deployment cover comprises markings which direct a user to apply pressure to a region of the needle assembly.

8. The needle assembly of claim 1, wherein the needle guide further comprises an adhesive layer adjacent the needle to impede horizontal and vertical movement of the needle assembly during use.

9. The needle assembly of claim 8, further comprising:
   a protective needle cover removably disposed over the needle guide adhesive layer, the protective needle cover maintaining a sterile environment for the needle, reaction region of the analyte reaction assembly, sensor strip and needle guide.

10. The needle assembly of claim 1, wherein the needle guide has a thickness that affects the depth of penetration of the needle during use.

11. The needle assembly of claim 1, wherein the sample comprises blood or dermal interstitial fluid.

12. The needle assembly of claim 1, wherein the needle is about 0.2 mm to 1.0 mm in length and about 25 gauge to 35 gauge in diameter.

13. The needle assembly of claim 1, wherein the volume of the sample is about 0.3 microliters to about 30 microliters.

14. The needle assembly of claim 1, wherein the analyte in the sample is at least one of glucose, lactate, fructosamine, glutamine, 3-hydroxybutyric acid, acetyl choline, amylase, bilirubin, alanine transaminase, aspartate transaminase, alkaline phosphatase, luteinizing hormone, chorionic gonadotropin, creatine kinase, creatinine, hemoglobin, myoglobin, albumin, troponin, cholesterol, a coagulate, C-reactive protein, proBNP, uric acid, pyruvate, a hormone, a sugar, a ketone, peroxide, prostate-specific antigen, prothrombin, fibrinogen, thromboplastin, thyroid stimulating hormone, an antibiotic, a drug, a bacterium and a virus.

15. The needle assembly of claim 1, wherein a reaction reagent in the sensor strip is at least one of glucose oxidase and glucose dehydrogenase.

16. The needle assembly of claim 1, wherein a reaction reagent in the sensor strip is carinactivase-1 and calcium ions.

17. The needle assembly of claim 16, wherein the reaction reagent in the sensor strip further includes an indicator.

18. The needle assembly of claim 17, wherein the indicator in the sensor strip is at least one of a peptidylarginine p-nitroanilide or peptidyl-7-amido-4-methylcoumarin.

* * * * *